United States Patent
Hoshino

(10) Patent No.: US 8,748,549 B2
(45) Date of Patent: Jun. 10, 2014

(54) FLUORINATED COMPOUND, FLUORINATED POLYMER AND FLUORINATED COPOLYMER

(71) Applicant: Asahi Glass Company, Limited, Chiyoda-ku (JP)

(72) Inventor: Taiki Hoshino, Chiyoda-ku (JP)

(73) Assignee: Asahi Glass Company, Limited, Chiyoda-ku (JP)

( * ) Notice: Subject to any disclaimer, the term of this patent is extended or adjusted under 35 U.S.C. 154(b) by 8 days.

(21) Appl. No.: 13/718,194

(22) Filed: Dec. 18, 2012

(65) Prior Publication Data

US 2013/0123447 A1    May 16, 2013

Related U.S. Application Data

(60) Division of application No. 13/432,744, filed on Mar. 28, 2012, now Pat. No. 8,471,056, which is a continuation of application No. PCT/JP2010/069521, filed on Nov. 2, 2010.

(30) Foreign Application Priority Data

Nov. 2, 2009   (JP) ................................. 2009-252410

(51) Int. Cl.
   *C08F 22/18*   (2006.01)
(52) U.S. Cl.
   USPC ............ 526/242; 560/130; 560/145; 570/127
(58) Field of Classification Search
   CPC ....................................................... C08F 22/18
   USPC ................................... 526/242; 560/130, 145
   See application file for complete search history.

(56) References Cited

U.S. PATENT DOCUMENTS

| | | | |
|---|---|---|---|
| 3,366,667 A | 1/1968 | Porret et al. | |
| 3,763,127 A | 10/1973 | Dolinski et al. | |
| 4,920,190 A | 4/1990 | Lina et al. | |
| 5,250,376 A * | 10/1993 | Kato et al. | 430/49.7 |
| 5,565,607 A | 10/1996 | Maekawa et al. | |
| 5,646,222 A | 7/1997 | Maekawa et al. | |
| 7,276,623 B2 | 10/2007 | Harada et al. | |
| 7,700,800 B2 | 4/2010 | Yamaguchi et al. | |
| 2010/0055608 A1 | 3/2010 | Ohashi et al. | |
| 2010/0143844 A1* | 6/2010 | Takeshita et al. | 430/285.1 |
| 2012/0165487 A1 | 6/2012 | Hoshino | |
| 2012/0190809 A1 | 7/2012 | Hoshino | |
| 2013/0005924 A1 | 1/2013 | Hoshino | |

FOREIGN PATENT DOCUMENTS

| | | |
|---|---|---|
| JP | 06-293705 | 10/1994 |
| JP | 2006-267183 | 10/2006 |
| WO | WO 91/19773 A1 | 12/1991 |
| WO | 02/083809 | 10/2002 |
| WO | 2004/035708 | 4/2004 |
| WO | 2006/098487 | 9/2006 |
| WO | 2010104188 A1 | 9/2010 |

OTHER PUBLICATIONS

Rouette, Encyclopedia of Textile Finishing, 2001, Woodhead Publishing, p. 45.*
Extended European Search Report issued Dec. 5, 2013, in Patent Application No. 10826916.8.
International Search Report issued Feb. 22, 2011 in PCT/JP2010/069521 filed Nov. 2, 2010.

* cited by examiner

*Primary Examiner* — Nicole M Buie-Hatcher
(74) *Attorney, Agent, or Firm* — Oblon, Spivak, McClelland, Maier & Neustadt, L.L.P.

(57) ABSTRACT

To provide a fluorinated compound having an $R^F$ group with at most 6 carbon atoms, whereby a fluorinated polymer having a highly durable water/oil repellency can be produced, and an environmental load is little, and a fluorinated polymer and a fluorinated copolymer having a highly durable water/oil repellency and presenting little environmental load, obtainable by polymerizing such a fluorinated compound. A fluorinated compound represented by the following formula (I) and its polymer:

$$CH_2=C(M)COO(CH_2)_nPhCOO(CH_2)_mC_rF_{2r+1} \quad (I)$$

(in the formula (I), M is a hydrogen atom, a methyl group or a halogen atom, n is an integer of from 0 to 2, Ph is a phenylene group, m is an integer of from 1 to 4, and r is an integer of from 1 to 6).

20 Claims, No Drawings

FLUORINATED COMPOUND, FLUORINATED POLYMER AND FLUORINATED COPOLYMER

CROSS-REFERENCE TO RELATED APPLICATIONS

This application is a divisional of U.S. patent application Ser. No. 13/432,744, filed Mar. 28, 2012, which is a continuation of PCT Application No. PCT/JP2010/069521, filed Nov. 2, 2010, which is based upon and claims the benefit of priority from Japanese Patent Application No. 2009-252410 filed on Nov. 2, 2009. The contents of those applications are incorporated herein by reference in their entirety.

TECHNICAL FIELD

The present invention relates to a novel fluorinated compound, a fluorinated polymer and fluorinated copolymer obtainable by polymerizing it.

BACKGROUND ART

As a technique to simultaneously impart water repellency and oil repellency to a surface, it is known to treat an article with an organic solvent solution or aqueous dispersion of a polymer comprising polymerized units of a polymerizable monomer containing a polyfluoroalkyl group (a group having a structure wherein at least two and at most all of hydrogen atoms in an alkyl group are substituted by fluorine atoms, such a polyfluoroalkyl group will be hereinafter referred to as an "$R^f$ group") in its molecule, or a copolymer of such a monomer with another monomer.

Such water/oil repellency is attributable to formation of "a low surface energy surface" having a low critical surface tension on the surface due to a surface orientation of $R^f$ groups on the coating film. It has been taken for granted that in order to attain both water repellency and oil repellency, orientation of $R^f$ groups at the surface is important, and in order to realize the surface orientation of $R^f$ groups, it is necessary to have constituting units derived from a monomer having a perfluoroalkyl group (a group having a structure wherein all of hydrogen atoms in an alkyl group are substituted by fluorine atoms, such a perfluoroalkyl group will be hereinafter referred to as an "$R^F$ group") with at least 8 carbon atoms in the polymer.

However, recently, EPA (Environmental Protection Agency in U.S.A.) has pointed out that a compound having an $R^F$ group with at least 8 carbon atoms is likely to be decomposed in vivo and in the natural environment, and the decomposed product is likely to be accumulated, i.e. its environment load is high. Therefore, a copolymer for a water/oil repellent composition is required, which has constituting units derived from a monomer having an $R^F$ group with at most 6 carbon atoms and containing no structural units derived from a monomer having an $R^F$ group with at least 8 carbon atoms.

However, in the case of a monomer having an $R^f$ group with at most 6 carbon atoms, as compared with a monomer having an $R^f$ group with at least 8 carbon atoms, the $R^f$ orientation at the surface tends to be weak, and the water/oil repellency tends to be low. Therefore, it is known to increase the water/oil repellency even in the case of a monomer having an $R^f$ group with at most 6 carbon atoms, by copolymerizing it with a monomer not having an $R^f$ group and having a high microcrystallite melting point (Patent Document 1), or copolymerizing it with a monomer having a crosslinkable functional group and not having an $R^f$ group (Patent Document 2).

On the other hand, with a polymer composed solely of a monomer having an $R^f$ group with at most 6 carbon atoms, it has been so far impossible to impart a sufficient water/oil repellency and excellent durability thereof.

Therefore, with respect to a monomer having an $R^f$ group with at most 6 carbon atoms, particularly an $R^F$ group with at most 6 carbon atoms, a monomer and its polymer have been desired, whereby by polymerizing such a monomer, it is possible to obtain a polymer having a highly durable water/oil repellency.

PRIOR ART DOCUMENTS

Patent Documents

Patent Document 1: WO02/083809
Patent Document 2: WO04/035708

DISCLOSURE OF INVENTION

Technical Problem

It is an object of the present invention to provide a fluorinated compound having an $R^F$ group with at most 6 carbon atoms, whereby a fluorinated polymer having a highly durable water/oil repellency can be produced, and an environmental load is little, and a fluorinated polymer having a highly durable water/oil repellency and presenting little environmental load, obtainable by polymerizing such a fluorinated compound.

Solution to Problem

The present invention provides the following.
(1) A fluorinated compound represented by the following formula (I):

$$CH_2=C(M)COO(CH_2)_nPhCOO(CH_2)_mC_rF_{2r+1} \quad (I)$$

(in the formula (I), M is a hydrogen atom, a methyl group or a halogen atom, n is an integer of from 0 to 2, Ph is a phenylene group, m is an integer of from 1 to 4, and r is an integer of from 1 to 6).
(2) The fluorinated compound according to the above (1), wherein Ph in the formula (I) is a 1,4-phenylene group.
(3) The fluorinated compound according to the above (1) or (2), wherein r in the formula (I) is an integer of from 2 to 6.
(4) The fluorinated compound according to the above (3), wherein r in the formula (I) is an integer of from 4 to 6.
(5) The fluorinated compound according to the above (1), wherein the fluorinated compound represented by the formula (I) is a compound represented by any one of the following formulae (I-1) to (I-7):

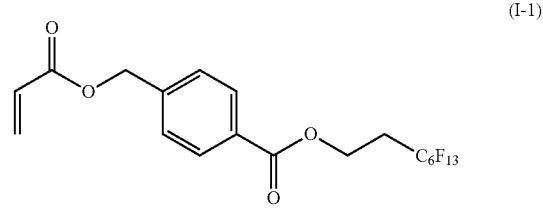

(I-1)

-continued

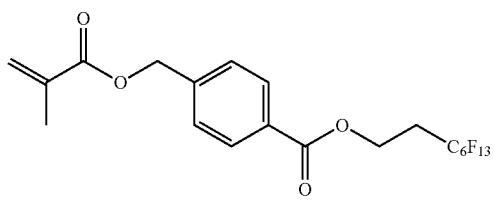

(I-2)

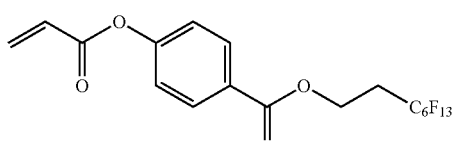

(I-3)

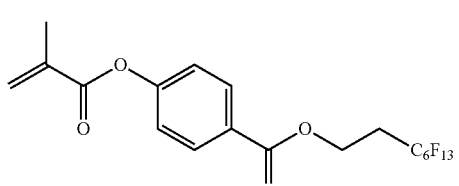

(I-4)

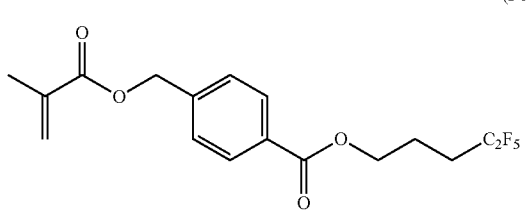

(I-5)

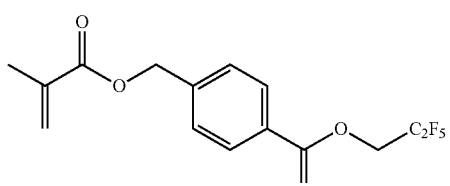

(I-6)

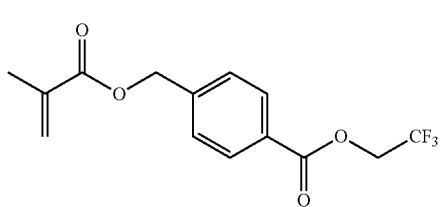

(I-7)

(6) The fluorinated compound according to any one of the above (1) to (5), wherein in the formula (I), r is an integer of from 4 to 6, and $C_rF_{2r+1}$ is linear.

(7) A fluorinated polymer obtainable by polymerizing one member selected from the fluorinated compound as defined in any one of the above (1) to (6).

(8) The fluorinated polymer according to the above (7), which has a mass average molecular weight (Mw) of from 2,000 to 1,000,000.

(9) The fluorinated polymer according to the above (8), which has a mass average molecular weight (Mw) of from 5,000 to 500,000.

(10) A fluorinated copolymer comprising from 10 to 99 mass % of structural units based on the fluorinated compound as defined in any one of the above (1) to (6) and from 1 to 90 mass % of structural units based on other monomer (X).

(11) The fluorinated copolymer according to the above (10), wherein the structural units based on other monomer (X) comprise structural units based on a halogenated olefin and structural units based on a monomer having a cross-linkable functional group and having no polyfluoroalkyl group.

Advantageous Effects of Invention

By using the fluorinated compound of the present invention, it is possible to produce a fluorinated polymer having a highly durable water/oil repellency and presenting little load to the environment. Further, the fluorinated polymer and fluorinated copolymer of the present invention have a highly durable water/oil repellency and present little load to the environment.

DESCRIPTION OF EMBODIMENTS

Now, embodiments of the present invention will be described. In this specification, (meth)acrylate means an acrylate or a methacrylate. Likewise, (meth)acrylic acid means acrylic acid or methacrylic acid.

<Fluorinated Compound of the Present Invention>

The fluorinated compound of the present invention is a fluorinated compound which, as shown in the following formula (I), has an acryloyloxy group (which may be substituted) as a polymerizable group at its one terminal and an $R^F$ group with at most 6 carbon atoms at the other terminal and which has, as a bivalent linking group to link the two, a linking group containing one benzene ring directly bonded to ester bonds. A fluorinated polymer obtainable by polymerizing the fluorinated compound of the present invention having such a molecular structure, has a water/oil repellency and also has a high durability whereby the water/oil repellency will not be impaired by e.g. use for a long period of time.

$$CH_2=C(M)COO(CH_2)_nPhCOO(CH_2)_mC_rF_{2r+1} \quad (I)$$

(in the formula (I), M is a hydrogen atom, a methyl group or a halogen atom, n is an integer of from 0 to 2, Ph is a phenylene group, m is an integer of from 1 to 4, and r is an integer of from 1 to 6).

In the above formula (I), M is a hydrogen atom, a methyl group or a halogen atom, and as the halogen atom, it specifically represents F, Cl, Br or the like. Preferred M is a hydrogen atom or a methyl group, and more preferred is a methyl group. In a case where M is a hydrogen atom, the obtainable polymer has a water/oil repellency and is particularly excellent in the durability to maintain the water/oil repellency. In a case where M is a methyl group, the obtainable polymer is particularly excellent in the initial water/oil repellency and also excellent in the durability to maintain the water/oil repellency.

In the above formula (I), n is an integer of from 0 to 2, but a preferred number of n is 0 or 1. When the number of n is 0 or 1, the raw material is readily available, such being desirable.

In the above formula (I), Ph is a phenylene group. It may be any one of a 1,2-phenylene group, a 1,3-phenylene group and a 1,4-phenylene group, so long as it is a phenylene group. However, in the present invention, Ph is preferably a 1,4- phenylene group, whereby the hydrophilic esters are present as being apart from each other.

Further, in the above formula (I), m is an integer of from 1 to 4, but a preferred number of m is from 1 to 3. When the number of m is from 1 to 3, the raw material is readily available, such being desirable.

Further, in the above formula (I), r is an integer of from 1 to 6. When r is within a range of from 1 to 6, the obtainable polymer shows a water/oil repellency, but in order to obtain a higher water/oil repellency, r is preferably from 2 to 6, more preferably from 4 to 6.

In the present invention, among fluorinated compounds represented by the above formula (I), a compound represented by any one of the following formulae (I-1) to (I-7) is particularly preferred.

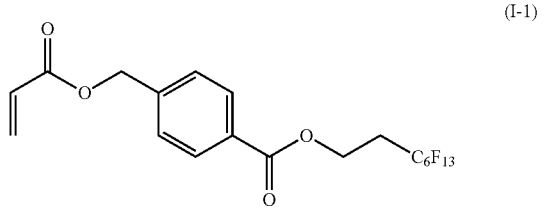
(I-1)

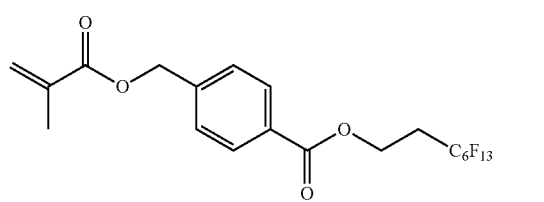
(I-2)

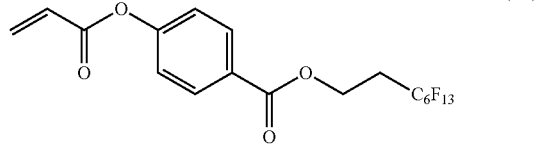
(I-3)

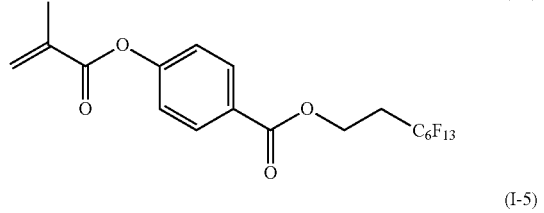
(I-4)

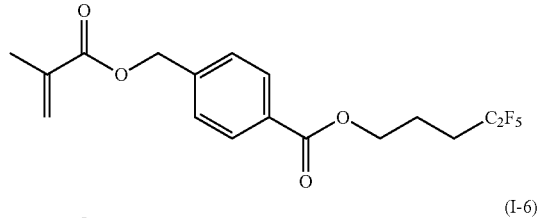
(I-5)

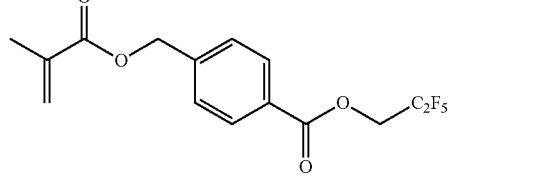
(I-6)

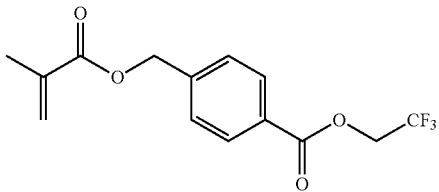
(I-7)

In the present invention, it is preferred that in the above formula (I), r is an integer of from 4 to 6, and $C_rF_{2r+1}$ is linear. Further, the $R^F$ group in the above formulae (I-1) to (I-4) is preferably linear.

<Production Method>

In the present invention, a method for producing the fluorinated compound represented by the above formula (I) is not particularly limited. As a method for producing the fluorinated compound represented by the above formula (I), specifically, the following production methods may, respectively, be mentioned for the following respective compounds (i) and (ii) which are different in n in the formula (I).

Fluorinated compound (i) of the above formula (I) wherein n is other than 0.

Fluorinated compound (ii) of the above formula (I) wherein n is 0.

(1) Method for producing fluorinated compound (i) of the above formula (I) wherein n is other than 0

The above fluorinated compound (i) can be produced, for example, by carrying out reactions 1-1 and 1-2 which will be described below, although not limited thereto. Here, in the following production process, identification of the obtainable intermediate substances or desired substances may be carried out by common methods such as measurement $^1$H-NMR (nuclear magnetic resonance analysis), FT-IR (Fourier transform infrared spectroscopy), elemental analyses, etc. Further, also in the case of producing the fluorinated compound (ii) in the after-described (2), identification of the obtainable intermediate substances or desired substances may be carried out by similar methods.

<Reaction 1-1>

Using, as a starting material, a compound represented by the formula $Y^1(CH_2)_nPhCOY^2$ (wherein $Y^1$ is Cl, Br or I, $Y^2$ is Cl, a hydroxy group or an alkoxy group, and Ph and n are as defined above), a compound (A) ($Y^1(CH_2)_nPhCOO(CH_2)_m C_rF_{2r+1}$, wherein $Y^1$, Ph, n, m and r are as defined above) is obtained by reacting a compound having an $R^F$ group (perfluoroalkyl group) with at most 6 carbon atoms thereto, as shown by the following reaction formula.

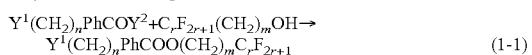

$$Y^1(CH_2)_nPhCOY^2 + C_rF_{2r+1}(CH_2)_mOH \rightarrow Y^1(CH_2)_nPhCOO(CH_2)_mC_rF_{2r+1} \quad (1\text{-}1)$$

In the above reaction 1-1, in the case of using a compound wherein $Y^2$ is Cl, i.e. an acid chloride, as the starting material, such a reaction is preferably carried out in the presence of an alkali. As the alkali, triethylamine, potassium carbonate or sodium hydroxide may, for example, be used. In such a case, the reaction 1-1 is preferably carried out in a solvent. As the solvent, specifically, acetone, 2-butanone, acetonitrile, ethyl acetate, methylene chloride, chloroform, pyridine or water may, for example, be mentioned.

In the above reaction 1-1, in the case of using an acid chloride wherein $Y^2$ is Cl, as the above starting material, specifically, the reaction is carried out under preferred reaction conditions among the following reaction conditions, by mixing the alkali (such as triethylamine) in a proportion of from 25 to 100 parts by mass, and the solvent in a proportion of from 50 to 5,000 parts by mass, to 100 parts by mass in total of the above starting material and the compound having an $R^F$ group with at most 6 carbon atoms. In a case where the solvent is pyridine, pyridine serves also as an alkali, and therefore, it is not required to add an alkali. In a case where the solvent is water (Schotten-Baumann reaction), a catalyst such as N-methylimidazole or 4-(dimethylamino)pyridine may, for example, be used as the case requires.

As the reaction conditions, preferably, conditions such as reaction container: made of glass, made of SUS, etc., temperature: from 0 to 40° C., pressure: from 0 to 1 MPa, atmosphere: in an atmosphere substituted by an inert gas such as nitrogen, argon or the like, time: from 1 to 24 hours, etc. may be mentioned. Here, the pressure as a reaction condition is not the absolute pressure in the reaction and represents the range of pressure to be used for pressurizing or depressurizing. Hereinafter, the same applies to the pressure as a reaction condition in this specification.

In the above reaction 1-1, in the case of using, as a starting material, a compound wherein $Y^2$ is a hydroxy group or an alkoxy group, as the catalyst, sulfuric acid or p-toluenesulfonic acid may, for example, be used. In such a case, the reaction 1-1 is carried out in the absence of a solvent or in a solvent, and as the solvent, specifically, toluene or 2-butanone may, for example, be mentioned.

In the above reaction 1-1, in the case of using a compound wherein $Y^2$ is a hydroxy group or an alkoxy group, as the above starting material, specifically, the reaction is carried out under preferred reaction conditions among the following reaction conditions, by mixing the catalyst (such as sulfuric acid) in a proportion of from 0.01 to 10 parts by mass, and the solvent in a proportion of from 0 to 5,000 parts by mass, to 100 parts by mass in total of the above starting material and the compound having an $R^F$ group with at most 6 carbon atoms.

As the reaction conditions, preferably, conditions such as reaction container: made of glass, made of SUS, etc., temperature: from 50 to 150° C., pressure: from –0.1 to 1 MPa, atmosphere: in an atmosphere substituted by an inert gas such as nitrogen, argon or the like, time: from 1 to 100 hours, etc. may be mentioned. Further, it is preferred to carry out the reaction while distilling reaction byproducts off, as the case requires.

As a method for purifying the compound (A) from the reaction crude liquid containing the compound (A) thus obtained, a method may, for example, be mentioned wherein to the reaction crude liquid, dichloropentafluoropropane, chloroform or ethyl acetate may, for example, be added, followed by washing a few times with a sufficient amount of distilled water, and then, the solvent is distilled off.

<Reaction 1-2>

To the compound (A) obtained in the above reaction 1-1, (meth)acrylic acid is reacted, as shown by the following reaction formula, to obtain a fluorinated compound (I) ($CH_2$=C(M)COO$(CH_2)_n$PhCOO$(CH_2)_m C_r F_{2r+1}$, wherein M, Ph, n, m and r are as defined above), which is the fluorinated compound (I) of the present invention wherein n is other than 0.

$$Y^1(CH_2)_nPhCOO(CH_2)_mC_rF_{2r+1}+CH_2=C(M)COOH \rightarrow CH_2=C(M)COO(CH_2)_nPhCOO(CH_2)_mC_rF_{2r+1} \quad (1\text{-}2)$$

The above reaction 1-2 is preferably carried out in the presence of an alkali. As the alkali, potassium carbonate, sodium carbonate or triethylamine may, for example, be preferably used. The reaction 1-2 is preferably carried out in a solvent. As the solvent, specifically, N,N-dimethylformamide (DMF), acetonitrile, acetone or 2-butanone may, for example, be used.

Specifically, the reaction 1-2 is carried out under preferred reaction conditions among the following reaction conditions, by mixing the alkali (such as potassium carbonate) in a proportion of from 20 to 200 parts by mass, and the solvent in a proportion of from 50 to 5,000 parts by mass, and further, as the case requires, a suitable amount of a polymerization inhibitor such as hydroquinone, to 100 parts by mass in total of the above compound (A) and the (meth)acrylic acid.

As the reaction conditions, preferably, conditions such as reaction container: made of glass, made of SUS, etc., temperature: from 40 to 150° C., pressure: from 0 to 1 MPa, time: from 1 to 50 hours, etc. may be mentioned.

As a method for purifying the fluorinated compound (i) from the reaction crude liquid containing the fluorinated compound (i) thus obtained, a method may, for example, be mentioned wherein to the reaction crude liquid, dichloropentafluoropropane, chloroform or ethyl acetate may, for example, be added, followed by washing a few times with a sufficient amount of distilled water, and then, the solvent is distilled off.

(2) Method for producing fluorinated compound (ii) of the above formula (I) wherein n is 0

The above fluorinated compound (ii) may be produced, for example, by carrying out the following reactions 2-1 and 2-2, although not limited thereto.

<Reaction 2-1>

Using, as a starting material, a compound represented by the formula HOPhCOOY$^5$ (wherein Y$^5$ is a hydrogen atom or a $C_{1-4}$ alkyl group), a compound (B) (HOPhCOO$(CH_2)_m C_r F_{2r+1}$, wherein Ph, m and r are as defined above) is obtained by reacting a compound having an $R^F$ group (perfluoroalkyl group) with at most 6 carbon atoms thereto, as shown by the following reaction formula.

$$HOPhCOOY^5+C_rF_{2r+1}(CH_2)_mOH \rightarrow HOPhCOO(CH_2)_mC_rF_{2r+1} \quad (2\text{-}1)$$

In the above reaction 2-1, it is preferred to use 4-toluenesulfonic acid monohydrate, sulfuric acid or the like, as a catalyst. The reaction 2-1 is carried out in the absence of a solvent or in a solvent, and as the solvent, specifically, toluene or 2-butanone may, for example, be used.

Specifically, the reaction 2-1 is carried out under preferred reaction conditions among the following reaction conditions, by mixing the catalyst (such as 4-toluenesulfonic acid monohydrate) in a proportion of from 0.01 to 10 parts by mass, and the solvent in a proportion of from 0 to 5,000 parts by mass, to 100 parts by mass in total of the above starting material and the compound having an $R^F$ group with at most 6 carbon atoms.

As the reaction conditions, preferably, conditions such as reaction container: made of glass, made of SUS, etc., temperature: from 50 to 150° C., pressure: from –0.1 to 1 MPa, atmosphere: in an atmosphere substituted by an inert gas such as nitrogen, argon or the like, time: from 1 to 100 hours, etc. may be mentioned. Further, it is preferred to carry out the reaction while distilling reaction byproducts off, as the case requires.

As a method for purifying the compound (B) from the reaction crude liquid containing the compound (B) thus obtained, a method may, for example, be mentioned wherein from the reaction crude liquid, an excess raw material component is distilled off, and to the obtained residue, chloroform, 2-butanone or the like is added, and the compound (B) is recrystallized.

<Reaction 2-2>

To the compound (B) obtained by the above reaction 2-1, a (meth)acrylic acid compound is reacted as shown by the following reaction formula to obtain a fluorinated compound (ii) $(CH_2=C(M)COOPhCOO(CH_2)_mC_rF_{2r+1}$, wherein M, Ph, m and r are as defined above) wherein n is 0 among the fluorinated compound (I) of the present invention.

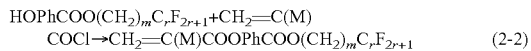

$HOPhCOO(CH_2)_mC_rF_{2r+1}+CH_2=C(M)$
$COCl \rightarrow CH_2=C(M)COOPhCOO(CH_2)_mC_rF_{2r+1}$ (2-2)

The above reaction 2-2 is preferably carried out in the presence of an alkali. As the alkali, triethylamine, potassium carbonate or sodium hydroxide may, for example, be used. The reaction 2-2 is preferably carried out in a solvent. As the solvent, specifically, methylene chloride, chloroform, acetone, 2-butanone, ethyl acetate, pyridine or water may, for example, be mentioned.

Specifically, the reaction 2-2 is carried out under preferred reaction conditions among the following reaction conditions, by mixing the alkali (such as triethylamine) in a proportion of from 25 to 100 parts by mass, and the solvent in a proportion of from 50 to 5,000 parts by mass, and further, as the case requires, a suitable amount of a polymerization inhibitor such as a hydroquinone, to 100 parts by mass in total of the above compound (B) and the (meth)acrylic acid compound. In a case where the solvent is pyridine, pyridine serves also as an alkali, and therefore, it is not required to add another alkali. In a case where the solvent is water (Schotten-Baumann reaction), a catalyst such as N-methylimidazole or 4-(dimethylamino)pyridine may, for example, be used, as the case requires.

As the reaction conditions, preferably, conditions such as reaction container: made of glass, made of SUS, etc., temperature: from 0 to 40° C., pressure: from 0 to 1 MPa, atmosphere: in an atmosphere substituted by an inert gas such as nitrogen, argon or the like, time: from 1 to 24 hours, etc. may be mentioned.

As a method for purifying the fluorinated compound (ii) from the reaction crude liquid containing the fluorinated compound (ii) thus obtained, a method may, for example, be mentioned wherein the reaction crude liquid is washed a few times with a sufficient amount of distilled water, and then, the solvent is distilled off.

<Polymer of the Present Invention>

The polymer of the present invention is a homopolymer obtainable by polymerizing one member selected from the above-described fluorinated compound of the present invention.

The polymer of the present invention preferably has a mass average molecular weight (Mw) of from 2,000 to 1,000,000, more preferably from 5,000 to 500,000. The polymer having a mass average molecular weight (Mw) within such a range is advantageous from the viewpoint of the durability of the water/oil repellency.

Here, the mass average molecular weight (Mw) of the polymer in this specification is a molecular weight calculated as a polymethyl methacrylate, which is measured by gel permeation chromatography (GPC).

As a method for polymerizing the fluorinated compound of the present invention, it is possible to employ a polymerization method such as an ion polymerization method or a radical polymerization method. Particularly, a radical polymerization method is preferred in that the polymerization can be carried out under a mild condition by using a radical initiator as the polymerization initiator. Specifically, the radical polymerization can be carried out by using a polymerization method such as suspension polymerization, solution polymerization, bulk polymerization or emulsion polymerization.

Among these polymerization methods, in the production of the polymer according to the present invention, it is preferred to employ a polymerization method wherein the polymerization is carried out in a medium in the presence of a polymerization initiator, and it is more preferred to employ a solution polymerization employing a solvent as the above medium, or an emulsion polymerization to be carried out by using a medium containing a surfactant and water.

The production of the polymer is specifically one to polymerize the monomer in a medium in the presence of a polymerization initiator.

Further, in the production of the polymer, the monomer concentration in the medium is preferably from 5 to 50 vol %, more preferably from 20 to 40 vol %, by volume percentage of the monomer to the medium. As the medium, a halogen compound, a hydrocarbon, a ketone, an ester or an ether may, for example, be mentioned.

As the halogen compound, a halogenated hydrocarbon or a halogenated ether may, for example, be mentioned. As the halogenated hydrocarbon, a hydrochlorofluorocarbon or a hydrofluorocarbon may, for example, be mentioned.

As the hydrochlorofluorocarbon, $CH_3CCl_2F$, $CHCl_2CF_2CF_3$ or $CHClFCF_2CClF_2$ may, for example, be mentioned.

As the hydrofluorocarbon, $CF_3CHFCHFCF_2CF_3$, $CF_3(CF_2)_4CHF_2$, $CF_3CF_2CF_2CH_2CH_2CH_3$, $CF_3(CF_2)_5CH_2CH_3$ or 1,1,2,2,3,3,4-heptafluorocyclopentane may, for example, be mentioned.

As the halogenated ether, a hydrofluoroether may, for example, be mentioned.

As the hydrofluoroether, $CF_3CF_2CF_2CF_2OCH_3$, $(CF_3)_2CFCF_2OCH_3$, $CF_3CF_2CF_2CF_2OCH_2CH_3$, $(CF_3)CFCF_2OCH_2CH_3$, $CF_3CF_2CF(OCH_3)CF(CF_3)_2$, $CF_3CF_2CF(OCH_2CH_3)CF(CF_3)_2$, $C_3H_7OCF(CF_3)CF_2OCH_3$, $CHF_2CF_2OCH_2CF_3$ or $CF_3CF_2CH_2OCF_2CHF_2$ may, for example, be mentioned.

As the hydrocarbon, an aliphatic hydrocarbon, an alicyclic hydrocarbon or an aromatic hydrocarbon may, for example, be mentioned.

As the aliphatic hydrocarbon, pentane, 2-methylbutane, 3-methylpentane, hexane, 2,2-dimethylbutane, 2,3-dimethylbutane, heptane, octane, 2,2,4-trimethylpentane, 2,2,3-trimethylhexane, decane, undecane, dodecane, 2,2,4,6,6-pentamethylheptane, tridecane, tetradecane or hexadecane may, for example, be mentioned.

As the alicyclic hydrocarbon, cyclopentane, methylcyclopentane, cyclohexane, methylcyclohexane or ethylcyclohexane may, for example, be mentioned.

As the aromatic hydrocarbon, benzene, toluene or xylene may, for example, be mentioned.

As the ketone, acetone, methyl ethyl ketone, 2-pentanone, 3-pentanone, 2-hexanone or methyl isobutyl ketone may, for example, be mentioned.

As the ester, methyl acetate, ethyl acetate, butyl acetate, methyl propionate, methyl lactate, ethyl lactate or pentyl lactate may, for example, be mentioned.

As the ether, diisopropyl ether, dioxane or tetrahydrofuran may, for example, be mentioned.

As the radical polymerization initiator, a commonly used initiator such as an azo type polymerization initiator, a peroxide type polymerization initiator or a redox type initiator may be used depending upon the polymerization temperature. As the radical polymerization initiator, an azo type compound is particularly preferred, and in a case where the polymerization is carried out in an aqueous medium, a salt of an azo type compound is more preferred.

The amount of the polymerization initiator to be added is preferably from 0.05 to 5 parts by mass, more preferably from 0.1 to 3 parts by mass, per 100 parts by mass of the monomer.

At the time of polymerization of a monomer, a molecular weight-adjusting agent may be used. As the molecular weight-adjusting agent, an aromatic compound, a mercapto alcohol or a mercaptan is preferred, and an alkyl mercaptan is particularly preferred. As such a molecular weight-adjusting agent, specifically, mercapto ethanol, n-octyl mercaptan, n-dodecyl mercaptan, t-dodecyl mercaptan or stearyl mercaptan may, for example, be mentioned.

The amount of the molecular weight-adjusting agent to be added is preferably from 0.01 to 5 parts by mass, more preferably from 0.1 to 3 parts by mass, per 100 parts by mass of the monomer.

The polymerization temperature is preferably from 20 to 150° C., more preferably from 40 to 120° C. As other polymerization conditions, conditions similar to ones used for polymerization for a usual (meth)acrylate type polymer may be applied. For example, the polymerization may be carried out in a nitrogen atmosphere, or an operation such as shaking may be added, such being preferred conditions in the production method of the present invention. With respect to the polymerization time, the polymer of the present invention can be obtained by carrying out the polymerization for from about 2 to 24 hours, although it may depend also on other polymerization conditions such as the polymerization temperature.

Further, in order to obtain the polymer of the present invention to have the above-mentioned preferred molecular weight range i.e. a range of from 2,000 to 1,000,000, more preferably from 5,000 to 500,000, by mass average molecular weight (Mw), the conditions such as the monomer concentration, the amount of the polymerization initiator, the polymerization temperature, the amount of the molecular weight-adjusting agent, etc. may be adjusted within the above-described preferred ranges. In general, under such a polymerization condition that the monomer concentration is high (low), the amount of the polymerization initiator is small (large), the polymerization temperature is low (high) or the amount of the molecular weight-adjusting agent is small (large), the molecular weight tends to be large (small).

Although the reason is not clearly understood, in the polymer of the present invention, $R^F$ groups are surface-oriented on the surface of a coating film by an interaction due to $\pi$-$\pi$ stacking of a benzene ring contained in the linking group of the fluorinated compound by using the fluorinated compound of the present invention as the monomer. By the surface orientation of $R^F$ groups, even by a monomer having an $R^F$ group with at most 6 carbon atoms, it is possible to impart a high water/oil repellency.

<Copolymer of the Present Invention>

The copolymer of the present invention is a fluorinated copolymer comprising from 10 to 99 mass % of structural units based on the above-described fluorinated compound of the present invention and from 1 to 90 mass % of structural units based on other monomer (X).

Other monomer (X) may, for example, be a halogenated olefin, a monomer having a crosslinkable group and having no polyfluoroalkyl group, and other monomer (Y).

As the halogenated olefin, a chlorinated olefin or a fluorinated olefin is preferred. Specifically, vinyl chloride, vinylidene chloride, tetrafluoroethylene or vinylidene fluoride is more preferred, and in consideration of the interaction with a substrate, vinyl chloride or vinylidene chloride is particularly preferred. By having structural units based on a halogenated olefin, the strength of the coating film made of the copolymer will be improved, and the adhesion between the coating film made of the copolymer and the substrate will be improved.

In the monomer having a crosslinkable functional group and having no polyfluoroalkyl group, the crosslinkable functional group is preferably a functional group having at least one bond among a covalent bond, an ionic bond and a hydrogen bond, or a functional group capable of forming a crosslinkable structure by an interaction with such a bond. By having a monomer having a crosslinkable functional group and having no polyfluoroalkyl group, the thermal resistance or abrasion resistance of the coating film of the fluorinated copolymer will be improved.

As such a functional group, an isocyanate group, a blocked isocyanate group, an alkoxysilyl group, an amino group, an alkoxymethylamide group, a silanol group, an ammonium group, an amide group, an epoxy group, a hydroxy group, an oxazoline group, a carboxy group, an alkenyl group or a sulfonic acid group may, for example, be preferred. Particularly preferred is an epoxy group, a hydroxy group, a blocked isocyanate group, an alkoxysilyl group, an amino group or a carboxy group.

As the monomer having a crosslinkable functional group and having no polyfluoroalkyl group, a (meth)acrylate, an acrylamide, a vinyl ether or a vinyl ester is preferred.

The following compounds may be mentioned as the monomer having a crosslinkable functional group and having no polyfluoroalkyl group.

2-Isocyanatoethyl(meth)acrylate, 3-isocyanatopropyl(meth)acrylate, 4-cyanatobutyl(meth)acrylate, a 2-butanoneoxime adduct of 2-isocyanatoethyl(meth)acrylate, a pyrazole adduct of 2-isocyanatoethyl(meth)acrylate, a 3,5-dimethylpyrazole adduct of 2-isocyanatoethyl(meth)acrylate, a 3-methylpyrazole adduct of 2-isocyanatoethyl(meth)acrylate, an ε-caprolactam adduct of 2-isocyanatoethyl(meth)acrylate, a 2-butanoneoxime adduct of 3-isocyanatopropyl(meth)acrylate, a pyrazole adduct of 3-isocyanatopropyl(meth)acrylate.

A 3,5-dimethylpyrazole adduct of 3-isocyanatopropyl(meth)acrylate, a 3-methylpyrazole adduct of 3-isocyanatopropyl(meth)acrylate, an ε-caprolactam adduct of 3-isocyanatopropyl(meth)acrylate, 2-butanoneoxime adduct of 4-isocyanatobutyl(meth)acrylate, a pyrazole adduct of 4-isocyanatobutyl(meth)acrylate, a 3,5-dimethylpyrazole adduct of 4-cyanatobutyl(meth)acrylate, a 3-methylpyrazole adduct of 4-cyanatobutyl(meth)acrylate, an ε-caprolactam adduct of 4-isocyanatobutyl(meth)acrylate.

Methoxymethyl(meth)acrylamide, ethoxy methyl(meth)acrylamide, butoxymethyl(meth)acrylamide, diacetone acrylamide, 3-methacryloyloxypropyl trimethoxysilane, trimethoxyvinylsilane, vinyltrimethoxysilane, dimethylaminoethyl(meth)acrylate, diethylaminoethyl(meth)acrylate, dimethylaminopropyl(meth)acrylate, (meth)acryloylmorpholine, (meth)acryloyloxyethyltrimethylammonium chloride, (meth)acryloyloxypropyltrimethylammonium chloride, (meth)acrylamidoethyltrimethylammonium chloride, (meth)acrylamidopropyltrimethylammonium chloride.

t-Butyl(meth)acrylamidesulfonic acid, (meth)acrylamide, N-methyl(meth)acrylamide, N-methylol(meth)acrylamide, N-butoxymethyl(meth)acrylamide, diacetone(meth)acrylamide, glycidyl(meth)acrylate, 2-hydroxyethyl(meth)acrylate, 2-hydroxypropyl(meth)acrylate, 4-hydroxybutyl(meth)acrylate, 3-chloro-2-hydroxypropyl methacrylate, polyoxyalkylene glycol mono(meth)acrylate, (meth)acrylic acid, 2-(meth)acryloyloxyethylsuccinic acid, 2-(meth)acryloyloxyhexahydrophthalic acid, 2-(meth)acryloyloxyethyl acid phosphate, allyl(meth)acrylate, 2-vinyl-2-oxazoline, a polycaprolacton ester of 2-vinyl-4-methyl-(2-vinyloxazoline)hydroxyethyl(meth)acrylate.

Tri(meth)allyl isocyanurate (T(M)AIC, manufactured by Nippon Kasei Chemical Co., Ltd.), triallyl cyanurate (TAC, manufactured by Nippon Kasei Chemical Co., Ltd.), phenylglycidyl ethyl acrylate tolylene diisocyanate (AT-600, manufactured by Kyoeisha Chemical Co., Ltd.), 3-(methyl ethyl ketoxime) isocyanatomethyl-3,5,5-trimethylcyclohexyl(2-hydroxyethyl methacrylate) cyanate (TECHCOAT HE-6P, manufactured by Kyoken Kasei).

As the monomer having a crosslinkable functional group and having no polyfluoroalkyl group, preferred are N-methylol(meth)acrylamide, N-butoxymethyl(meth)acrylamide, 2-hydroxyethyl(meth)acrylate, 4-hydroxybutyl(meth)acrylate, a 3,5-dimethylpyrazole adduct of 3-isocyanatopropyl (meth)acrylate, diacetone acrylamide, glycidyl methacrylate, a polycaprolacton ester of hydroxyethyl(meth)acrylate AT-600 (manufactured by Kyoeisha Chemical Co., Ltd.), and TECHCOAT HE-6P (manufactured by Kyoken Kasei).

Other monomer (Y) is not particularly limited so long as it is copolymerizable with the fluorinated compound of the present invention as a base to form the essential structural units of the copolymer of the present invention. Further, if it is such a monomer that is capable of imparting preferred other properties without substantially impairing the effects of the copolymer of the present invention when polymerized units based on the monomer (Y) are introduced into the copolymer of the present invention with its content properly adjusted, such a monomer is not particularly limited. As the monomer (Y), two or more types of monomer (Y) may be used.

The following compounds may be mentioned as such other monomer (Y).

Methyl(meth)acrylate, ethyl(meth)acrylate, propyl(meth)acrylate, butyl(meth)acrylate, n-hexyl(meth)acrylate, cyclohexyl(meth)acrylate, 2-ethylhexyl(meth)acrylate, benzyl (meth)acrylate, octyl(meth)acrylate, decyl(meth)acrylate, lauryl(meth)acrylate, cetyl(meth)acrylate, stearyl(meth)acrylate, behenyl(meth)acrylate, 3-ethoxypropyl(meth)acrylate, methoxybutyl(meth)acrylate, 2-ethylbutyl(meth)acrylate, 1,3-dimethylbutyl(meth)acrylate, 2-methylpentyl (meth)acrylate.

Vinyl acetate, vinyl propionate, butene, isoprene, butadiene, ethylene, propylene, vinyl ethylene, pentene, ethyl-2-propylene, butylethylene, cyclohexylpropylethylene, decylethylene, dodecylethylene, hexene, isohexylethylene, neopentylethylene, (1,2-diethoxycarbonyl)ethylene, (1,2-dipropoxycarbonyl)ethylene, methoxyethylene, ethoxyethylene, butoxyethylene, 2-methoxypropylene, pentyloxyethylene, cyclopentanoyloxyethylene, cyclopentylacetoxyethylene, styrene, α-methylstyrene, p-methylstyrene, hexylstyrene, octylstyrene, nonylstyrene.

N,N-dimethyl(meth)acrylamide, vinyl alkyl ether, halogenated alkyl vinyl ether, vinyl alkyl ketone, aziridinylethyl (meth)acrylate, 2-ethylhexylpolyoxyalkylene(meth)acrylate, polyoxyalkylene(meth)acrylate.

A crotonic acid alkyl ester, a maleic acid alkyl ester, a fumaric acid alkyl ester, a citraconic acid ester, a masaconic acid alkyl ester, triallyl cyanurate, allyl acetate, N-vinylcarbazole, maleimide, N-methylmaleimide, a (meth)acrylate having silicone in its side chain, a (meth)acrylate having an urethane bond, a (meth)acrylate having a polyoxyalkylene chain wherein the terminal is a $C_{1-4}$ alkyl group, an alkylene di(meth)acrylate, etc.

The proportion of the structural units based on the fluorinated compound in the copolymer is from 10 to 99 mass %, preferably from 20 to 95 mass %, particularly preferably from 50 to 90 mass %.

The proportion of the structural units based on other monomer (X) in the copolymer is from 1 to 90 mass %, preferably from 5 to 80 mass %, particularly preferably from 10 to 40 mass %.

In a case where the copolymer contains, as other monomer (X), a halogenated olefin, a monomer having a crosslinkable functional group and having no polyfluoroalkyl group, etc., the proportion of the structural units based on the halogenated olefin is preferably from 1 to 40 mass %, more preferably from 3 to 30 mass %, particularly preferably from 5 to 30 mass %, from the viewpoint of the adhesion to the substrate. Further, the proportion of the structural units based on the monomer having a crosslinkable functional group and having no polyfluoroalkyl group is preferably from 0.5 to 10 mass %, more preferably from 1 to 5 mass %, particularly preferably from 1 to 3 mass %, from the viewpoint of the water/oil repellency and its durability.

Structural units based on other monomer (Y) may be contained in the copolymer in a proportion within a range not to impair the properties of the copolymer. In consideration of the effects of the present invention, the proportion of other monomer (Y) is preferably from 0 to 40 mass %, more preferably from 0 to 30 mass %, particularly preferably from 0 to 20 mass %.

The mass average molecular weight (Mw) of the copolymer of the present invention is the same as the mass average molecular weight of the above-described polymer, and the preferred embodiments are also the same.

As a polymerization method for the copolymer of the present invention, the same polymerization method may be used as the above-described method for polymerizing the fluorinated compound, and the preferred embodiments are also the same.

Specifically, the respective monomers are copolymerized in a solvent in the presence of a polymerization initiator and, as the case requires, a surfactant.

As the structural units based on the fluorinated compound in the copolymer of the present invention, the above-described fluorinated compound of the present invention may be used in the same manner, and the preferred embodiments are also the same.

As the medium, the same medium as in the case of producing the above polymer may be used. Further, in the case of emulsion polymerization, water or a mixed solvent of water with an aqueous solvent, is preferred.

The aqueous solvent may, for example, be ethylene glycol, propylene glycol, diethylene glycol, dipropylene glycol, tripropylene glycol or dipropylene glycol.

The surfactant may, for example, be a hydrocarbon type surfactant or a fluorinated surfactant, and each may, for example, be an anionic surfactant, a nonionic surfactant, a cationic surfactant or an amphoteric surfactant.

As the surfactant, from the viewpoint of the dispersion stability, a combined use of a nonionic surfactant with a cationic surfactant or an amphoteric surfactant, or a single use of an anionic surfactant is preferred, and a combined use of a nonionic surfactant with a cationic surfactant is more preferred.

The total amount of surfactants is preferably from 1 to 20 parts by mass, more preferably from 1 to 15 parts by mass, per the total (100 parts by mass) of the respective monomers.

The radial polymerization initiator, the molecular weight-adjusting agent, the amounts of the molecular weight-adjusting agent, etc., the polymerization temperature and the polymerization time, may be the same as in the above-described method for producing the polymer. Preferred embodiments are also the same. The amount of the polymerization initiator to be incorporated is preferably from 0.05 to 5 parts by mass, more preferably from 0.1 to 3 parts by mass, per the total (100 parts by mass) of the respective monomers.

The amount of the molecular weight-adjusting agent to be added is preferably from 0.01 to 5 parts by mass, more preferably from 0.1 to 3 parts by mass, per the total amount (100 parts by mass) of the respective monomers.

Further, in order to obtain the copolymer of the present invention to have the above-mentioned preferred molecular weight range i.e. a range of from 2,000 to 1,000,000, more preferably from 5,000 to 500,000, by mass average molecular weight (Mw), the conditions such as the monomer concentrations, the amount of the polymerization inhibitor, the polymerization temperature, the amount of the molecular weight-adjusting agent, etc. may be adjusted within the above-described preferred ranges.

EXAMPLES

Now, Examples of the present invention will be given, but it should be understood that the present invention is by no means restricted by such Examples.

<1> Production of Fluorinated Compound

Example 1

Into a reactor (internal capacity: 300 mL, made of glass) equipped with a stirrer and a dropping funnel, linear $C_6F_{13}CH_2CH_2OH$ (48.2 g), triethylamine (16.1 g), and acetone (100 mL) were put and stirred. Then, by an ice bath, the inner temperature of the reactor was adjusted to be at most 10° C., and in a nitrogen atmosphere, a solution of 4-(chloromethyl)benzoic acid chloride (25.0 g) in acetone (20 mL) was dropwise added. Further, the temperature was returned to room temperature, and stirring was continued for 2 hours.

The obtained reaction crude liquid was transferred to a separating funnel, dichloropentafluoropropane (tradename: AK-225, manufactured by Asahi Glass Company, Limited, hereinafter sometimes referred to as AK-225) (100 mL) was added, followed by washing three times with distilled water (100 mL), and the solvent in the AK-225 phase was distilled off to obtain 66.6 g of a compound (A-1) (white solid) represented by the following structural formula (A-1) and classified into the above compound (A). The yield was 95%.

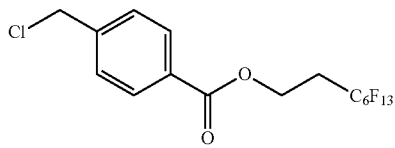
(A-1)

The measured results of $^1$H-NMR of the obtained compound (A-1) are shown below. Here, each measured value means a measured value derived from a group shown in ( ) following the measured value, but in a case where this group has a portion defined by [ ], the measured value means a measured value derived from the portion defined by [ ]. Hereinafter, the same applies to all of the measured results of NMR shown in Examples.

$^1$H-NMR (solvent: CDCl$_3$) δ(ppm): 2.62 (2H, m, —CH$_2$CF$_2$—), 4.62 (2H, s, ClCH$_2$—), 4.64 (2H, t, —OCH$_2$—), 7.48 (2H, d, Ph), 8.03 (2H, d, Ph).

Into a reactor (internal capacity: 100 mL, made of glass) equipped with a stirrer and a dropping funnel, acrylic acid (2.00 g), potassium carbonate (4.60 g) and DMF (20 mL) were put and stirred. Then, heating was carried out so that the inner temperature of the reactor became 50° C., and a solution of the compound (A-1) (14.3 g) in DMF (10 mL) was dropwise added. The dropping funnel was replaced by a Dimroth condenser, and the reactor was heated to 80° C., followed by stirring for 2 hours.

The obtained reaction crude liquid was transferred to a separating funnel, AK-225 (50 mL) was added, followed by washing three times with distilled water (50 mL), and the solvent in the AK-225 phase was distilled off to obtain 14.8 g of the fluorinated compound (I-1) of the present invention (white solid) represented by the following formula (I-1). The yield was 95%.

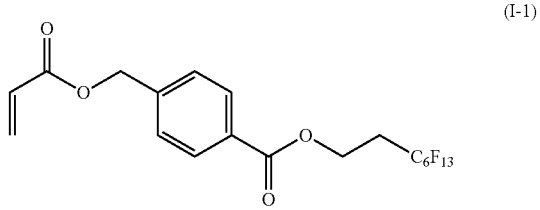
(I-1)

The measured results of $^1$H-NMR of the obtained fluorinated compound (I-1) of the present invention are shown below.

$^1$H-NMR (solvent: CDCl$_3$) δ (ppm): 2.62 (2H, m, —CH$_2$CF$_2$—), 4.64 (2H, t, —COO[CH$_2$]CH$_2$—), 5.26 (2H, s, —COO[CH$_2$]Ph-), 5.90 (1H, d, transC=CH$_2$), 6.19 (1H, dd, —CH=), 6.48 (1H, d, cisC=CH$_2$), 7.46 (2H, d, Ph), 8.04 (2H, d, Ph).

Example 2

Into a reactor (internal capacity: 100 mL, made of glass) equipped with a stirrer and a dropping funnel, methacrylic acid (1.68 g), potassium carbonate (3.08 g) and DMF (20 mL) were put and stirred. Then, heating was carried out so that the inner temperature of the reactor became 50° C., and a solution of the compound (A-1) (9.60 g) in DMF (10 mL) was dropwise added. The dropping funnel was replaced by a Dimroth condenser, and the reactor was heated to 80° C. and stirred for 2 hours.

The obtained reaction crude liquid was transferred to a separating funnel, AK-225 (50 mL) was added, followed by washing three times with distilled water (50 mL), and the solvent in the AK-225 phase was distilled off to obtain 0.1 g of a fluorinated compound (I-2) of the present invention (pale yellow liquid) represented by the following structural formula (I-2). The yield was 96%.

(I-2)

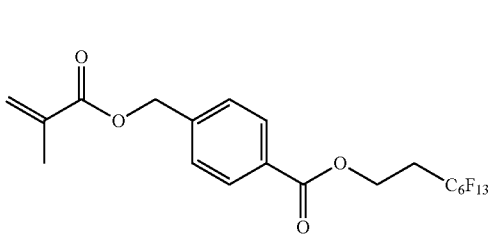

The measured results of ¹H-NMR of the obtained fluorinated compound (I-2) of the present invention are shown below.

¹H-NMR (solvent: CDCl₃) δ (ppm): 1.99 (3H, s, —CH₃), 2.61 (2H, m, —CH₂CF₂—), 4.64 (2H, t, —COO[CH₂]CH₂—), 5.25 (2H, s, —COO[CH₂]Ph-), 5.63 (1H, s, transC=CH₂), 6.19 (1H, s, cisC=CH₂), 7.45 (2H, d, Ph), 8.04 (2H, d, Ph).

Example 3

Into a reactor (internal capacity: 200 mL, made of glass) equipped with a stirrer, in a nitrogen atmosphere, methyl 4-hydroxybenzoate (25.0 g), 4-toluenesulfonic acid monohydrate (3.13 g) and linear C₆F₁₃CH₂CH₂OH (119.7 g) were put and stirred. Then, heating was carried out so that the inner temperature of the reactor became 120° C., the reactor was depressurized (from 0 to −0.05 MPa), and stirring was continued for 6 hours while distilling methanol off. Further, by lowering the depressurizing degree, excess C₆F₁₃CH₂CH₂OH was distilled off.

The obtained white solid was recrystallized from chloroform to obtain 71.5 g of a compound (B-1) (white solid) represented by the following structural formula (B-1) and classified into the above compound (B). The yield was 90%.

(B-1)

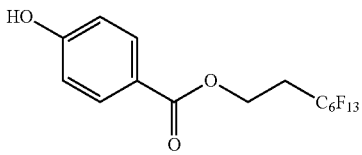

The measured results of ¹H-NMR of the obtained compound (B-1) are shown below.

¹H-NMR (solvent: CD₃COCD₃) δ (ppm): 2.81 (2H, m, —CH₂CF₂—), 4.62 (2H, t, —COO[CH₂]CH₂—), 6.94 (2H, d, Ph), 7.91 (2H, d, Ph), 9.21 (1H, s, —OH).

Into a reactor (internal capacity: 50 mL, made of glass) equipped with a stirrer and a dropping funnel, the compound (B-1) (10.0 g), triethylamine (2.51 g) and methylene chloride (20 mL) were put and stirred. Then, by an ice bath, the inner temperature of the reactor was adjusted to be at most 10° C., and in a nitrogen atmosphere, acrylic acid chloride (2.15 g) was dropwise added. Further, the temperature was returned to room temperature, and stirring was continued for 2 hours.

The obtained reaction crude liquid was transferred to a separating funnel, AK-225 (50 mL) was added, followed by washing three time with distilled water (20 mL), and the solvent in the AK-225 phase was distilled off to obtain 8.35 g of a fluorinated compound (I-3) of the present invention (white solid) represented by the following structural formula (I-3). The yield was 75%.

(I-3)

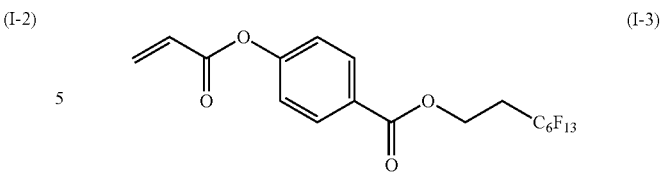

The measured results of ¹H-NMR of the obtained fluorinated compound (I-3) of the present invention are shown below.

¹H-NMR (solvent: CDCl₃) δ (ppm): 2.61 (2H, m, —CH₂CF₂—), 4.63 (2H, t, —COOCH₂—), 6.06 (1H, s, transC=CH₂), 6.33 (1H, dd, —CH=), 6.63 (1H, s, cisC=CH₂), 7.24 (2H, d, Ph), 8.09 (2H, d, Ph).

Example 4

Into a reactor (internal capacity: 50 mL, made of glass) equipped with a stirrer and a dropping funnel, the compound (B-1) (10.00 g), triethylamine (2.51 g) and methylene chloride (20 mL) were put and stirred. Then, by an ice bath, the inner temperature of the reactor was adjusted to be at most 10° C., and in a nitrogen atmosphere, methacrylic acid chloride (2.48 g) was dropwise added. Further, the temperature was returned to room temperature, and stirring was continued for 2 hours.

The obtained reaction crude liquid was transferred to a separating funnel and washed three time with distilled water (20 mL), and the solvent in the methylene chloride phase was distilled off to obtain 5.88 g of a fluorinated compound (I-4) of the present invention (white solid) represented by the following structural formula (I-4). The yield was 52%.

(I-4)

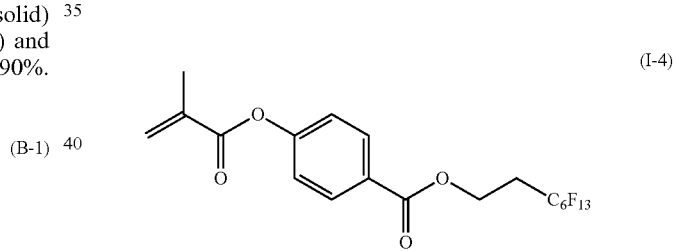

The measured results of ¹H-NMR of the obtained fluorinated compound (I-4) of the present invention are shown below.

¹H-NMR (solvent: CDCl₃) δ (ppm): 2.07 (3H, s, CH₃—), 2.61 (2H, m, —CH₂CF₂—), 4.63 (2H, t, —COOCH₂—), 5.80 (1H, s, transC=CH₂), 6.38 (1H, s, cisC=CH₂), 7.23 (2H, d, Ph), 8.08 (2H, d, Ph).

Example 5

Into a reactor (internal capacity: 200 mL, made of glass) equipped with a stirrer and a dropping funnel, C₂F₅CH₂CH₂CH₂OH (23.6 g), triethylamine (16.1 g) and acetone (80 mL) were put and stirred. Then, by an ice bath, the inner temperature of the reactor was adjusted to be at most 10° C., and in a nitrogen atmosphere, a solution of 4-(chloromethyl)benzoic acid chloride (25.0 g) in acetone (15 mL) was dropwise added. Further, the temperature was returned to room temperature, and stirring was continued for 2 hours.

The obtained reaction crude liquid was transferred to a separating funnel, AK-225 (100 mL) was added, followed by washing three times with distilled water (100 mL), and the solvent in the AK-225 phase was distilled off to obtain 40.2 g of a compound (A-2) (pale yellow liquid) represented by the following structural formula (A-2) and classified into the above compound (A). The yield was 93%.

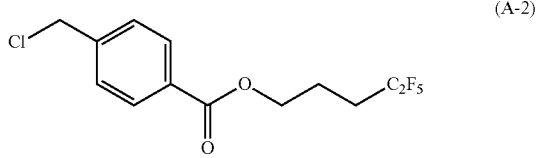
(A-2)

The measured results of ¹H-NMR and ¹⁹F-NMR of the obtained fluorinated compound (A-2) are shown below.

¹H-NMR (solvent: CDCl₃) δ (ppm): 2.05-2.31 (4H, m, —CH₂[CH₂CH₂]CF₂—), 4.41 (2H, t, —OCH₂—), 4.62 (2H, s, ClCH₂—), 7.48 (2H, d, Ph), 8.03 (2H, d, Ph).

¹⁹F-NMR (solvent: CDCl₃) δ (ppm): −85.9 (3F, s, —CF₃), −118.7 (2F, t, —CF₂—).

Into a reactor (internal capacity: 50 mL, made of glass) equipped with a stirrer and a dropping funnel, methacrylic acid (2.73 g), potassium carbonate (5.02 g) and DMF (20 mL) were put and stirred. Then, heating was carried out so that the inner temperature of the reactor became 50° C., and a solution of the compound (A-2) (10.0 g) in DMF (10 mL) was dropwise added. The dropping funnel was replaced with a Dimroth condenser, and the reactor was heated to 80° C. and stirred for 2 hours.

The obtained reaction crude liquid was transferred to a separating funnel, AK-225 (50 mL) was added, followed by washing three times with distilled water (50 mL), and the solvent in the AK-225 phase was distilled off to obtain 11.1 g of a fluorinated compound (I-5) of the present invention (pale yellow liquid) represented by the following structural formula (I-5). The yield was 97%.

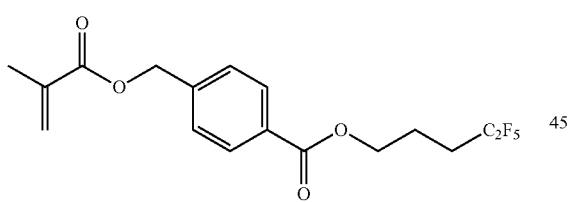
(I-5)

The measured results of ¹H-NMR and ¹⁹F-NMR of the obtained fluorinated compound (I-5) of the present invention are shown below.

¹H-NMR (solvent: CDCl₃) δ (ppm): 1.99 (3H, s, —CH₃), 2.05-2.31 (4H, m, —CH₂[CH₂CH₂]CF₂—), 4.40 (2H, t, —COO[CH₂]CH₂—), 5.26 (2H, s, —COO[CH₂]Ph-), 5.63 (1H, s, transC=CH₂), 6.19 (1H, s, cisC=CH₂), 7.46 (2H, d, Ph), 8.04 (2H, d, Ph).

¹⁹F-NMR (solvent: CDCl₃) δ (ppm): −85.9 (3F, s, —CF₃), −118.8 (2F, t, —CF₂—).

Example 6

Into a reactor (internal capacity: 200 mL, made of glass) equipped with a stirrer and a dropping funnel, C₂F₅CH₂OH (25.0 g), triethylamine (19.4 g) and acetone (60 mL) were put and stirred. Then, by an ice bath, the inner temperature of the reactor was adjusted to be at most 10° C., and in a nitrogen atmosphere, a solution of 4-(chloromethyl)benzoic acid chloride (33.1 g) in acetone (20 mL) was dropwise added. Further, the temperature was returned to room temperature, and stirring was continued for 2 hours.

The obtained reaction crude liquid was transferred to a separating funnel, AK-225 (100 mL) was added, followed by washing three times with distilled water (100 mL), and the solvent in the AK-225 phase was distilled off to obtain 49.9 g of a compound (A-3) (pale yellow solid) represented by the following structural formula (A-3) and classified into the above compound (A). The yield was 99%.

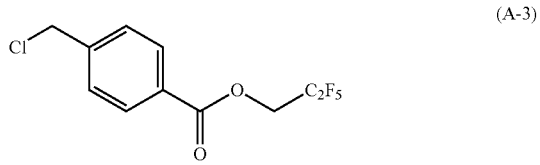
(A-3)

The measured results of ¹H-NMR of the obtained compound (A-3) are shown below.

¹H-NMR (solvent: CDCl₃) δ (ppm): 4.62 (2H, 2, ClCH₂—), 4.78 (2H, t, —OCH₂—), 7.50 (2H, d, Ph), 8.06 (2H, d, Ph).

Into a reactor (internal capacity: 50 mL, made of glass) equipped with a stirrer and a dropping funnel, methacrylic acid (2.99 g), potassium carbonate (5.50 g) and DMF (20 mL) were put and stirred. Then, heating was carried out so that the inner temperature of the reactor became 50° C., and a solution of the compound (A-3) (10.0 g) in DMF (10 mL) was dropwise added. The dropping funnel was replaced with a Dimroth condenser, and the reactor was heated to 80° C. and stirred for 2 hours.

The obtained reaction crude liquid was transferred to a separating funnel, AK-225 (50 mL) was added, followed by washing three times with distilled water (50 mL), and the solvent in the AK-225 phase was distilled off to obtain 6.95 g of a fluorinated compound (I-6) of the present invention (colorless transparent liquid) represented by the following structural formula (I-6). The yield was 60%.

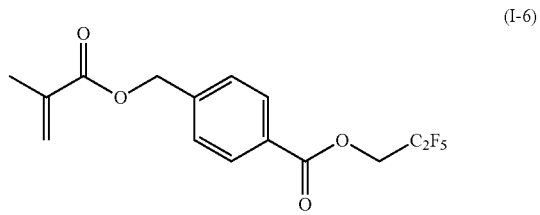
(I-6)

The measured results of ¹H-NMR of the obtained fluorinated compound (I-6) of the present invention are shown below.

¹H-NMR (solvent: CDCl₃) δ (ppm): 1.99 (3H, s, —CH₃), 4.77 (2H, t, —COOCH₂—), 5.26 (2H, s, —COO[CH₂]Ph-), 5.63 (1H, s, transC=CH₂), 6.19 (1H, s, cisC=CH₂), 7.47 (2H, d, Ph), 8.06 (2H, d, Ph).

Example 7

Into a reactor (internal capacity: 200 mL, made of glass) equipped with a stirrer and a dropping funnel, CF₃CH₂OH (20.0 g), triethylamine (23.26 g) and acetone (50 mL) were put and stirred. Then, by an ice bath, the inner temperature of the reactor was adjusted to be at most 10° C., and in a nitrogen atmosphere, a solution of 4-(chloromethyl)benzoic acid chloride (39.68 g) in acetone (20 mL) was dropwise added. Further, the temperature was returned to room temperature, and stirring was continued for 2 hours.

The obtained reaction crude liquid was transferred to a separating funnel, AK-225 (100 mL) was added, followed by washing three times with distilled water (100 mL), and the solvent in the AK-225 phase was distilled off to obtain 45.3 g of a compound (A-4) (pale yellow liquid) represented by the following structural formula (A-4) and classified into the above compound (A). The yield was 90%.

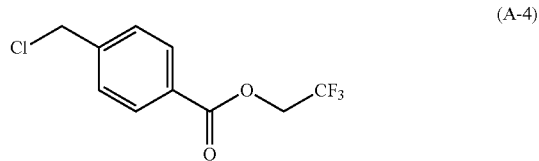 [SMILES: O=C(OCC(F)(F)F)c1ccc(CCl)cc1]

(A-4)

The measured results of $^1$H-NMR and $^{19}$F-NMR of the obtained compound (A-4) are shown below.

$^1$H-NMR (solvent: CDCl$_3$) δ (ppm): 4.62 (2H, s, ClCH$_2$—), 4.67 (2H, q, —OCH$_2$—), 7.48 (2H, d, Ph), 8.05 (2H, d, Ph).

Into a reactor (internal capacity: 50 mL, made of glass) equipped with a stirrer and a dropping funnel, methacrylic acid (3.58 g), potassium carbonate (6.57 g) and DMF (20 mL) were put and stirred. Then, heating was carried out so that the inner temperature of the reactor became 50° C., and a solution of the compound (A-4) (10.0 g) in DMF (5 mL) was dropwise added. The dropping funnel was replaced with a Dimroth condenser, and the reactor was heated to 80° C. and stirred for 2 hours.

The obtained reaction crude liquid was transferred to a separating funnel, AK-225 (50 mL) was added, followed by washing three times with distilled water (50 mL), and the solvent in the AK-225 phase was distilled off to obtain 10.8 g of a fluorinated compound (I-7) of the present invention (colorless transparent liquid) represented by the following structural formula (I-7). The yield was 90%.

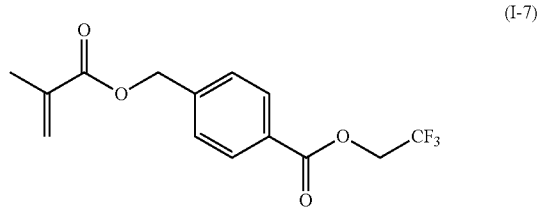 [SMILES: C=C(C)C(=O)OCc1ccc(C(=O)OCC(F)(F)F)cc1]

(I-7)

The measured results of $^1$H-NMR of the obtained fluorinated compound (I-7) of the present invention are shown below.

$^1$H-NMR (solvent: CDCl$_3$) δ (ppm): 1.99 (3H, s, —CH$_3$), 4.68 (2H, q, —COOCH$_2$—), 5.22 (2H, s, —COO[CH$_2$]Ph-), 5.63 (1H, s, transC=CH$_2$), 6.19 (1H, s, cisC=CH$_2$), 7.48 (2H, d, Ph), 8.08 (2H, d, Ph).

<2> Production of Polymer

Examples 8 to 14

Using the fluorinated compounds (I-1 to I-7) obtained in the above Examples as monomers, respectively, polymers were produced as follows.

Into a 30 mL glass ampoule for polymerization, a monomer, 2,2'-azobisisobutyronitrile as an initiator and AK-225 or a mixture of AK-225 and tetrahydrofuran (THF) as a solvent were put in the amounts as shown in Table 1. The gas in the interior of the ampoule was substituted by nitrogen gas, and then, the ampoule was sealed and maintained for 16 hours in a hot bath of 60° C. The solution containing the polymer was dropped into methanol of 20 times by mass, followed by stirring to let solid precipitate. The obtained solid was collected by filtration and vacuum-dried overnight at 60° C. to obtain a polymer in the amount shown by mass in Table 1. The molecular weight of the recovered polymer was measured by GPC. The mass average molecular weight (Mw) of the obtained polymer is shown in Table 1.

Here, the above mass average molecular weight (Mw) was measured by the following GPC measuring method.

(GPC Measuring Method)

The recovered polymer was dissolved in a mixed solvent of a fluorinated solvent (AK-225, manufactured by Asahi Glass Company, Limited)/hexafluoroisopropyl alcohol=99/1 (volume ratio) to obtain a 0.5 mass % solution, which was passed through a filter of 0.2 μm to obtain an analytical sample. With respect to such a sample, the number average molecular weight (Mn) and the mass average molecular weight (Mw) were measured. The measuring conditions were as follows.

Apparatus: HLC-8220GPC, manufactured by TOSOH CORPORATION,
Column: Two MIXED-E, manufactured by Polymer Laboratories, were connected in series,
Temperature for measurement: 37° C.,
Amount injected: 50 μL,
Exit velocity: 1 mL/min,
Standard sample: EasiCal PM-2, manufactured by Polymer Laboratories,
Eluent: Mixed solvent of fluorinated solvent (AK-225, manufactured by Asahi Glass Company, Limited)/hexafluoroisopropyl alcohol=99/1 (volume ratio).

TABLE 1

| | | Monomer | | Initiator | solvent | Polymer | | |
|---|---|---|---|---|---|---|---|---|
| Ex. No. | Symbol | Mass (g) | | Mass (mg) | Symbol | Mass (g) | Yield (g) | Mw |
| Ex. 8 | I-1 | 6.00 | | 18 | AK-225 | 24.0 | 5.29 | 124,000 |
| 9 | I-2 | 6.00 | | 17 | AK-225 | 24.0 | 5.55 | 258,000 |
| 10 | I-3 | 4.00 | | 12 | 225/THF | 16.0 | 3.64 | 7,000 |
| 11 | I-4 | 4.00 | | 12 | 225/THF | 16.0 | 3.88 | 94,000 |
| 12 | I-5 | 4.00 | | 17 | 225/THF | 16.0 | 3.56 | 111,000 |
| 13 | I-6 | 4.50 | | 21 | 225/THF | 10.5 | 4.14 | 129,000 |
| 14 | I-7 | 3.00 | | 8 | 225/THF | 12.0 | 2.77 | 84,000 |

Here, an abbreviation of the compound in Table 1 has the following meaning.

225/THF: A mixed solvent of AK-225 (50 mass %) and THF (50 mass %)<

<Evaluation>

With respect to each of the polymers obtained in Examples 8 to 14, a test plate was prepared by the following method, and the water/oil repellency was evaluated. The results are shown in Table 2.

[Preparation of Test Plate]

A obtained polymer was diluted with AK-225 so that the solid content concentration became 2.0 mass %, and the obtained polymer solution was used as a treating liquid. The polymer solution was applied by dip coating to three glass plates and dried at 150° C. for 10 minutes to obtain treated substrates each having a coating film formed on the surface.

[Water/Oil Repellency]

Using one of the above treated substrates, the contact angles of water and hexadecane on the coating film were measured, whereby the water/oil repellency of the coating film obtainable from the treating liquid containing the polymer prepared in each of the above Examples, was evaluated. Here, the measurements of the contact angles were carried out by means of CA-X, manufactured by Kyowa Interface Science Co., Ltd.

As results, the actually measured values of the contact angles as well as the results evaluated in accordance with the following standards, are shown in Table 2.

The water repellency was evaluated by three grades using the contact angle of water being 100° as the standard.

⊚ (contact angle: at least 110°): Excellent in water repellency

○ (contact angle: at least 90° and less than 110°): Water repellency observed x (contact angle: less than 90°): Inadequate in water repellency The oil repellency was evaluated by three grades using the contact angle of n-hexadecane being 50° as the standard.

⊚ (contact angle: at least 70°): Excellent in oil repellency

○ (contact angle: at least 40° and less than 70°): Oil repellency observed x (contact angle: less than 40°): Inadequate in oil repellency

[Dynamic Water Repellency]

Using one of the above treated substrates, the dynamic contact angles to water on the coating film was measured, whereby the dynamic water repellency of the coating film obtainable from the treating liquid containing a polymer prepared in each of the above Examples, was evaluated. Here, by means of DCAT21 (manufactured by DataPhysics), the receding contact angle to water was measured at 25° C. by Wilhelmy method. As results, the actually measured values of the receding contact angles as well as the results evaluated in accordance with the following standards, are shown in Table 2.

The dynamic water repellency was evaluated by three grades using the receding contact angle of water being 50° as the standard.

⊚ (contact angle: at least 80°): Excellent in dynamic water repellency

○ (contact angle: at least 50° and less than 80°): Dynamic water repellency observed x (contact angle: less than 50°): Inadequate in dynamic water repellency

[Durability]

Using one of the above treated substrates, such a substrate was immersed for 3 hours in distilled water of 40° C., whereupon from the change rate between the receding contact angle where no treatment was carried out and the receding contact angle after the treatment, the durability of the dynamic water repellency of the coating film was evaluated. As results, the actually measured values of the receding contact angles after the immersion as well as the results evaluated in accordance with the following standards, are shown in Table 2.

⊚ (change rate: less than 10%): Excellent in durability of dynamic water repellency ○ (change rate: at least 10% and less than 50%): Durability in dynamic water repellency observed x (change rate: at least 50%): Inadequate in durability of dynamic water repellency

TABLE 2

| | | Water/oil repellency | | | | Dynamic water repellency | | | |
| --- | --- | --- | --- | --- | --- | --- | --- | --- | --- |
| | | | | | | Receding | | Receding | |
| | Ex. No. | Contact angle (water) | Evaluation of water repellency | Contact angel (hexadecane) | Evaluation of oil repellency | contact angle (initial) | Evaluation of water repellency | contact angle (after immersion) | Evaluation of durability |
| Ex. | 8 | 116 | ⊚ | 81 | ⊚ | 58 | ○ | 57 | ⊚ |
| | 9 | 118 | ⊚ | 77 | ⊚ | 96 | ⊚ | 69 | ○ |
| | 10 | 116 | ⊚ | 75 | ⊚ | 88 | ⊚ | 88 | ⊚ |
| | 11 | 117 | ⊚ | 73 | ⊚ | 104 | ⊚ | 91 | ○ |
| | 12 | 108 | ○ | 53 | ○ | 81 | ⊚ | 65 | ○ |
| | 13 | 101 | ○ | 60 | ○ | 88 | ⊚ | 55 | ○ |
| | 14 | 91 | ○ | 42 | ○ | 83 | ⊚ | 65 | ○ |

As is evident from Table 2, it is possible to obtain a polymer having a highly durable water/oil repellency by using the fluorinated compound of the present invention.

Further, from these results, it can be said that in the case of a fluorinated compound of the present invention having the formula (I) wherein M is a hydrogen atom, the obtainable polymer has water/oil repellency and is particularly excellent in the durability to maintain such water/oil repellency. Further, it is evident that in the case of a fluorinated compound of the present invention having the formula (I) wherein M is a methyl group, the obtainable polymer is excellent particularly in the initial water/oil repellency and also excellent in the durability to maintain such water/oil repellency.

<3> Production of Copolymer

Using the fluorinated compounds (I-1 to I-4) of the present invention obtained in the above Examples as monomers, respectively, copolymers were produced as follows.
(Abbreviations)
(Monomers)
C6FMA: $CH_2=C(CH_3)COO(CH_2)_2C_6F_{13}$
VCM: Vinyl chloride
VdCl: Vinylidene chloride
IP: Isoprene
DOM: Dioctyl maleate
NMAM: N-methylolacrylamide
HEMA: 2-Hydroxyethyl methacrylate
(Surfactants)
PEO-20: Aqueous solution containing 10 mass % of polyoxyethylene oleyl ether (Emulgen E430, manufactured by Kao Corporation, about 26 mol ethylene oxide adduct)

TMAC: Aqueous solution containing 10 mass % of trimethylammonium chloride (ARQUAD 18-63, manufactured by Lion Corporation)

P-204: Aqueous solution containing 10 mass % of ethylene oxide propylene oxide polymer (tradename: Pronone 204, manufactured by NOF Corporation, proportion of ethylene oxide: 40 mass %)

(Molecular Weight-Adjusting Agent)

nDOSH: n-Dodecylmercaptan (Polymerization Initiator)

VA-061A: Aqueous solution containing 10 mass % of an acetate of 2,2'-azobis[2-(2-imidazolin-2-yl)propane] (VA-061, manufactured by Wako Pure Chemical Industries, Ltd.)

(Media)

DPG: Dipropylene glycol

Water: Ion-exchanged water

Example 15

Into a beaker made of glass, 38.0 g of I-2, 3.4 g of DOM, 1.5 g of NMAM, 0.5 g of nDOSH, 16.3 g of PEO-20, 2.7 g of TMAC, 2.7 g of P-204, 16.3 g of DPG and 64.5 g of water were put, heated at 50° C. for 30 minutes and then mixed by means of a homomixer (Biomixer, manufactured by Nissei Corporation) to obtain a mixed liquid.

The obtained mixed liquid was treated under 40 MPa by means of a high pressure emulsifier (Minilabo manufactured by APV Rannie) while maintaining the temperature at 50° C. to obtain an emulsion. The obtained emulsion was put into a stainless steel reactor and cooled to not higher than 40° C. Then, 2.7 g of VA-061A was added, and the gas phase was substituted by nitrogen, then 11.4 g of VCM was introduced, and with stirring, a polymerization reaction was carried out at 60° C. for 15 hours to obtain an emulsion of a copolymer. The proportions of the respective monomers in the monomer mixture, the solid content concentration (mass %) of the emulsion and the molecular weight of the copolymer are shown in Tables 3 and 4.

Examples 16 to 23

An emulsion of a copolymer was obtained in the same manner as in Example 15 except that the charged amounts of the respective materials were changed to the amounts shown in Table 3. However, the monomers VdCl and IP were added at the same timing as the polymerization initiator VA-061A. The proportions of the respective monomers in the monomer mixture, the solid content concentration (mass %) of the emulsion and the molecular weight of the copolymer are shown in Tables 3 and 4.

Comparative Example 1

An emulsion of a copolymer was obtained in the same manner as in Example 15 except that I-2 as the monomer was changed to C6FMA. The proportions of the respective monomers in the monomer mixture, the solid content concentration (mass %) of the emulsion and the molecular weight of the copolymer are shown in Tables 3 and 4.

<Physical Properties of Copolymer>

With respect to a copolymer recovered by the following recovery method, measurement of the molecular weight was carried out by the above-described GPC measuring method.

(Copolymer Recovery Method)

6 g of an emulsion was concentrated so that the solid content became about 40 mass % to obtain a concentrated liquid. To the concentrated liquid, about 10 g of tetrahydrofuran (hereinafter referred to as THF) was dropped to dissolve the solid in the concentrated liquid thereby to obtain a THF solution. In a case where dissolution was difficult, ultrasonic waves were applied. Then, the above THF solution was dropped into 60 g of methanol, followed by stirring to precipitate a solid. The obtained solid was recovered by reduced pressure filtration and vacuum-dried overnight at 35° C. to obtain a copolymer.

TABLE 3

| Charge (g) | | Example 15 | Example 16 | Example 17 | Example 18 | Example 19 | Example 20 | Example 21 | Example 22 | Example 23 | Comp. Ex. 1 |
|---|---|---|---|---|---|---|---|---|---|---|---|
| Monomers | I-1 | | | | | | 19.0 | | | | |
| | I-2 | 38.0 | | | | 19.0 | | | | | |
| | I-3 | | 38.0 | | | | | | | | |
| | I-4 | | | 38.0 | 28.5 | 19.0 | 19.0 | 35.3 | 19.0 | 23.6 | |
| | C6FMA | | | | 9.5 | | | | | | 38.0 |
| | VCM | 11.4 | 11.4 | 11.4 | 11.4 | 11.4 | 11.4 | 15.2 | | | 11.4 |
| | VdCl | | | | | | | | 4.5 | 1.4 | |
| | IP | | | | | | | | | 1.4 | |
| | DOM | 3.4 | 3.4 | 3.4 | 3.4 | 3.4 | 3.4 | 2.2 | | | 3.4 |
| | NMAM | 1.5 | 1.5 | 1.5 | 1.5 | 1.5 | 1.5 | 1.6 | | 0.8 | 1.5 |
| | HEMA | | | | | | | | 0.2 | | |
| Surfactants | PEO-20 | 16.3 | 16.3 | 16.3 | 16.3 | 16.3 | 16.3 | 16.3 | 7.1 | 8.1 | 16.3 |
| | TMAC | 2.7 | 2.7 | 2.7 | 2.7 | 2.7 | 2.7 | 2.7 | 1.2 | 1.4 | 2.7 |
| | P-204 | 2.7 | 2.7 | 2.7 | 2.7 | 2.7 | 2.7 | 2.7 | 1.2 | 1.4 | 2.7 |
| Molecular weight-adjusting agent | nDOSH | 0.5 | 0.5 | 0.5 | 0.5 | 0.5 | 0.5 | 0.5 | 0.5 | 0.5 | 0.5 |
| Polymerization initiator | VA-061A | 2.7 | 2.7 | 2.7 | 2.7 | 2.7 | 2.7 | 2.7 | 1.2 | 2.7 | 2.7 |
| Media | DPG | 16.3 | 16.3 | 16.3 | 16.3 | 16.3 | 16.3 | 16.3 | 7.1 | 8.1 | 16.3 |
| | Water | 64.5 | 64.5 | 64.5 | 64.5 | 64.5 | 64.5 | 64.5 | 28.3 | 31.1 | 64.5 |
| Solid content (mass %) | | 32.6 | 34.8 | 33.7 | 35.4 | 35.1 | 34.8 | 34.1 | 33.4 | 35.5 | 35.0 |
| Polymer | Mw | 15,600 | 21,300 | 18,300 | 17,900 | 14,800 | 17,000 | 19,900 | 61,400 | 92,300 | 16,800 |
| | Mn | 8,600 | 10,400 | 9,100 | 9,900 | 7,300 | 8,700 | 9,400 | 17,400 | 20,000 | 9,700 |

TABLE 4

| Structural units (mass %) | | 15 | 16 | 17 | 18 | 19 | 20 | 21 | 22 | 23 | Comp. Ex. 1 |
|---|---|---|---|---|---|---|---|---|---|---|---|
| Monomers | I-1 | | | | | | 35 | | | | |
| | I-2 | 70 | | | | 35 | | | | | |
| | I-3 | | 70 | | | | | | | | |
| | I-4 | | | 70 | 52.5 | 35 | 35 | 65 | 80 | 87 | |
| | C6FMA | | | | 17.5 | | | | | | 70 |
| | VCM | 21 | 21 | 21 | 21 | 21 | 21 | 28 | | | 21 |
| | VdCl | | | | | | | | 19 | 5 | |
| | IP | | | | | | | | | 5 | |
| | DOM | 6.3 | 6.3 | 6.3 | 6.3 | 6.3 | 6.3 | 4 | | | 6.3 |
| | NMAM | 2.7 | 2.7 | 2.7 | 2.7 | 2.7 | 2.7 | 3 | | 3 | 2.7 |
| | HEMA | | | | | | | | 1 | | |

<Evaluation>

With respect to each of the emulsions obtained in the above Example 15 to 23 and Comparative Example 1, a test cloth was prepared by the following method, and the water/oil repellency and heavy rain durability were evaluated. The results are shown in Tables 7 and 8.

[Preparation of Test Cloth]

An emulsion of a copolymer was diluted with distilled water to adjust the solid content concentration to be 1 mass %, and then, Sumitex Resin M-3 (manufactured by Sumitomo Chemical Co., Ltd.) as a thermal curing agent and Sumitex Accelerator ACX (manufactured by Sumitomo Chemical Co., Ltd.) as a thermal curing catalyst were added so that each concentration became 0.3 mass %, thereby to obtain a water/oil repellent composition.

In the water/oil repellent composition, a dyed nylon cloth or polyester cloth was immersed and the squeezed so that the wet pickup would be 70 mass % or 60 mass %. The wet cloth was dried at 110° C. for 90 seconds and then dried at 170° C. for 60 seconds to obtain a test cloth. With respect to such a test cloth, the water/oil repellency and heavy water durability were evaluated.

The results are shown in Tables 7 and 8. Here, in Tables 7 and 8, "–" for the number of washing times indicates that washing was not carried out at all.

[Oil Repellency]

With respect to the test cloth, the oil repellency was evaluated in accordance with a test method in AATCC-TM118-1966. The oil repellency is shown by grades in Table 5. A grade with +(–) shows that such a nature is slightly better (worse).

TABLE 5

| Oil repellency level | Test solution | Surface tension (25° C.) mN/m |
|---|---|---|
| 8 | n-Heptane | 20.0 |
| 7 | n-Octane | 21.8 |
| 6 | n-Decane | 23.5 |
| 5 | n-Dodecane | 25.0 |
| 4 | n-Tetradecane | 26.7 |
| 3 | n-Hexadecane | 27.3 |
| 2 | 65 Parts of nujol/35 parts of hexadecane | 29.6 |
| 1 | Nujol | 31.2 |
| 0 | One less than 1 | — |

[Water Repellency]

With respect to the test cloth, the water repellency was evaluated in accordance with a spray test in JIS L1092-1992. The water repellency is shown by grades in Table 6. A grade with +(–) shows that such a nature is slightly better (worse). That is, a grade with +(–) shows that such a nature is slightly better (worse) as compared with the standard level of that grade.

TABLE 6

| Water repellency level | State |
|---|---|
| 100 | No wetting or no deposition of water droplet observed on the surface |
| 90 | Deposition of water droplets slightly observed on the surface |
| 80 | Individual partial wetting observed on the surface |
| 70 | Wetting observed over a half of the surface |
| 50 | Wetting observed over the entire surface |
| 0 | Completely wetted |

With respect to the water repellency after washing, washing was repeated 20 times in accordance with the water washing method in the attachment 103 of JIS L0217. After the washing, the test cloth was air-dried overnight in a room at a room temperature of 25° C. under a relative humidity of 60%, whereupon the above water repellency was evaluated.

[Heavy Rain Durability]

In accordance with the method disclosed in JIS L1092(C) (Bundesmann test), rainfall was simulated under conditions of a rainfall of 100 cc/min, a rainwater temperature of 20° C. and a rainfall duration of 10 minutes. The water repellency immediately after the rainfall (initial stage) and water repellency after washing were evaluated. The water repellency was represented by five grades of from 1 to 5. The larger the number, the better the water repellency. A grade with +(–) shows that such a nature is slightly better (worse).

One with grade 3 or higher is regarded as exhibiting water repellency.

With respect to water repellency after washing, washing was repeated five times in accordance with the water washing method in the attachment 103 of JIS L0217, and then the test cloth was left to standstill overnight under conditions of a room temperature of 25° C. and a humidity of 55% and evaluated (hereinafter referred to as air-dried performance). Further, the test cloth was heat-dried at 120° C. for 60 seconds by a pin stenter and evaluated (hereinafter referred to as after heating performance).

TABLE 7

Cloth Nylon Evaluation

| | Oil repellency | Water repellency | Bundesmann test Number of washing time | | | |
|---|---|---|---|---|---|---|
| | | | — | | 5 | |
| | — | — | 20 | — | Air-dried performance | After heating performance |
| Ex. 15 | 5− | 100 | 70 | 4+ | 2− | 4 |
| Ex. 16 | 4 | 100 | 80 | 5− | 2− | 4+ |
| Ex. 17 | 5− | 100 | 70 | 4+ | 2− | 3+ |
| Ex. 18 | 4− | 100 | 70+ | 5− | 3 | 4 |
| Ex. 19 | 4− | 100 | 80− | 5− | 2− | 4 |
| Ex. 20 | 5− | 100 | 70− | 5− | 2− | 4− |
| Ex. 21 | 4 | 100 | 70 | 5− | 3 | 4 |
| Ex. 22 | 2 | 100− | 70 | 4+ | 3− | 4 |
| Ex. 23 | 5− | 100 | 70− | 5− | 2 | 3+ |
| Comp. Ex. 1 | 4 | 90+ | 50 | 1+ | 1 | 1+ |

TABLE 8

Cloth Polyester Evaluation

| | Oil repellency | Water repellency | Bundesmann test Number of washing time | | | |
|---|---|---|---|---|---|---|
| | | | — | | 5 | |
| | — | — | 20 | — | Air-dried performance | After heating performance |
| Ex. 15 | 5 | 100 | 80+ | 5− | 2− | 5− |
| Ex. 16 | 5+ | 100 | 80+ | 5 | 2− | 5− |
| Ex. 17 | 5− | 100 | 80 | 5− | 2 | 4 |
| Ex. 18 | 5− | 100 | 90− | 5 | 2 | 4 |
| Ex. 19 | 5− | 100 | 90− | 5 | 2− | 5− |
| Ex. 20 | 5 | 100 | 80+ | 5 | 2− | 4+ |
| Ex. 21 | 5− | 100 | 80 | 5− | 2 | 4 |
| Ex. 22 | 3− | 100 | 70+ | 5− | 3− | 4 |
| Ex. 23 | 5− | 100 | 70− | 5− | 2− | 4− |
| Comp. Ex. 1 | 6− | 100− | 80 | 1+ | 1 | 1+ |

INDUSTRIAL APPLICABILITY

The fluorinated compound of the present invention is a fluorinated compound having an $R^F$ group with at most 6 carbon atoms, which presents little environmental load, and a polymer obtainable by polymerizing it has a highly durable water/oil repellency. Accordingly, in place of a copolymer having an $R^F$ group with at least 8 carbon atoms presenting a high environmental load, it is useful for e.g. a water/oil repellent composition.

What is claimed is:

1. A fluorinated polymer comprising, in polymerized form, a fluorinated compound of formula (I):

$$CH_2=C(M)COO(CH_2)_nPhCOO(CH_2)_mC_rF_{2r+1} \quad (I)$$

wherein:
M is a hydrogen atom, a methyl group or a halogen atom;
n is an integer of 0 to 2;
Ph is a phenylene group;
m is an integer of 1 to 4; and
r is an integer of 1 to 6.

2. The fluorinated polymer of claim 1, having a mass average molecular weight of 2,000 to 1,000,000.

3. The fluorinated polymer of claim 1, having a mass average molecular weight of 5,000 to 500,000.

4. The fluorinated polymer of claim 1, consisting of, in polymerized form, the fluorinated compound of formula (I).

5. The fluorinated polymer of claim 1, wherein Ph is a 1,4-phenylene group.

6. The fluorinated polymer of claim 1, wherein r is an integer of 2 to 6.

7. The fluorinated polymer of claim 1, wherein r is an integer of 4 to 6.

8. The fluorinated polymer of claim 1, wherein the fluorinated compound of the formula (I) is a compound represented by any one of the following formulae (I-1) to (I-7):

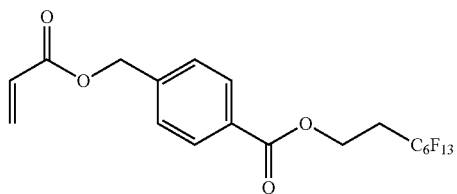

(I-1)

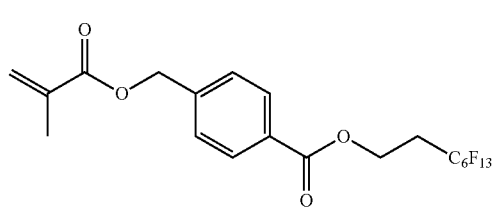

(I-2)

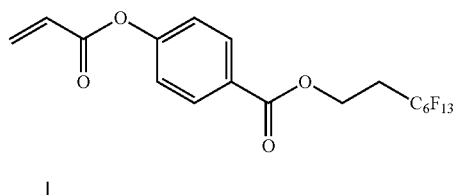

(I-3)

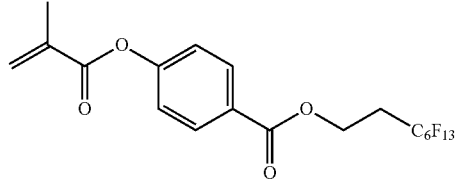

(I-4)

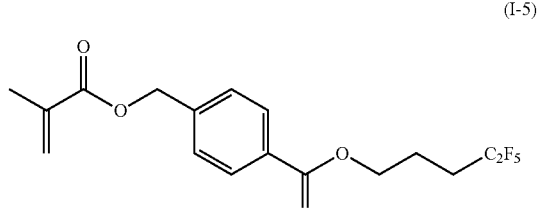

(I-5)

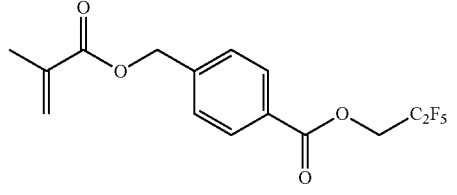

(I-6)

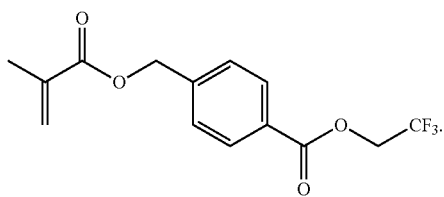 (I-7)

9. The fluorinated polymer of claim 1, wherein r is an integer of 4 to 6, and $C_rF_{2r+1}$ is linear.
10. The fluorinated polymer of claim 1, wherein M is a hydrogen atom.
11. The fluorinated polymer of claim 1, wherein M is a methyl group.
12. The fluorinated polymer of claim 1, wherein n is 0 or 1.
13. The fluorinated polymer of claim 1, wherein m is 1, 2 or 3.
14. The fluorinated polymer of claim 1, which is a copolymer comprising, in polymerized form,
    10 to 99 mass % of the fluorinated compound of formula (I), and
    1 to 90 mass % of another monomer X.
15. The fluorinated polymer of claim 14, wherein the other monomer X is selected from the group consisting of (i) a halogenated olefin, and (ii) a monomer having a cross-linkable functional group and having no polyfluoroalkyl group.
16. The fluorinated polymer of claim 14, wherein the other monomer X is a halogenated olefin selected from the group consisting of vinyl chloride, vinylidene chloride, tetrafluoroethylene, and vinylidene fluoride.
17. The fluorinated polymer of claim 14, wherein the other monomer X is a monomer having a cross-linkable functional group and having no polyfluoroalkyl group, wherein the cross-linkable functional group is selected from the group consisting of an isocyanate group, a blocked isocyanate group, an alkoxysilyl group, an amino group, an alkoxymethylamide group, a silanol group, an ammonium group, an amide group, an epoxy group, a hydroxy group, an oxazoline group, a carboxy group, an alkenyl group and a sulfonic acid group.
18. The fluorinated polymer of claim 14, wherein the other monomer X is selected from the group consisting of a (meth) acrylate, an acrylamide, a vinyl ether and a vinyl ester.
19. The fluorinated polymer of claim 1, which is a copolymer comprising, in polymerized form,
    20 to 95 mass % of the fluorinated compound of formula (I), and
    5 to 80 mass % of another monomer X.
20. The fluorinated polymer of claim 1, which is a copolymer comprising, in polymerized form,
    50 to 90 mass % of the fluorinated compound of formula (I), and
    10 to 40 mass % of another monomer X.

* * * * *